United States Patent [19]

King et al.

[11] 4,002,693

[45] Jan. 11, 1977

[54] PROCESS FOR THE PRODUCTION OF O-PHENYLPHENOL

[75] Inventors: Ian Robert King, Warrington; Anthony MacDonald Hildon, Linslade, Leighton Buzzard, both of England

[73] Assignee: Laporte Industries Limited, London, England

[22] Filed: Feb. 18, 1975

[21] Appl. No.: 550,768

[30] Foreign Application Priority Data

Feb. 28, 1974 United Kingdom ............ 9130/74

[52] U.S. Cl. .......................... 260/620; 260/586 C
[51] Int. Cl.$^2$ ................. C07C 45/00; C07C 37/06
[58] Field of Search ............ 260/621 H, 620, 586 C

[56] References Cited

UNITED STATES PATENTS

| | | | |
|---|---|---|---|
| 1,862,000 | 6/1932 | Britton et al. | 260/620 |
| 1,879,337 | 9/1932 | Laage | 260/621 H |
| 2,503,641 | 4/1950 | Taylor et al. | 260/621 H |
| 3,637,870 | 1/1972 | Berthoux et al. | 260/620 |

FOREIGN PATENTS OR APPLICATIONS

| | | | |
|---|---|---|---|
| 1,249,473 | 10/1971 | United Kingdom | 260/620 |

OTHER PUBLICATIONS

Freifelder, "Practical Catalytic Hydrogenation," pp. 35–39, John Wiley & Sons (1971).
Plesek, "Coll. Czech. Chem. Comm.," vol. 21, pp. 375–381, (1956).

Primary Examiner—Norman Morgenstern
Attorney, Agent, or Firm—Larson, Taylor and Hinds

[57] ABSTRACT

A method of preparing an o-phenyl phenol from a cyclohexanone which comprises the steps of forming an o-cyclohexenyl cyclohexanone from the cyclohexanone by condensing the cyclo-hexanone in the presence of an inherently sulphur-free condensation catalyst, and then dehydrogenating the resulting o-cyclohexenyl cyclohexanone by contacting the o-cyclohexenyl cyclohexanone with a dehydrogenation catalyst in the presence of sufficient sulphur in the form of elemental sulphur or an organo-sulphur compound to improve the selectivity of the dehydrogenation catalyst with respect to the formation of o-phenyl phenol.

9 Claims, 2 Drawing Figures

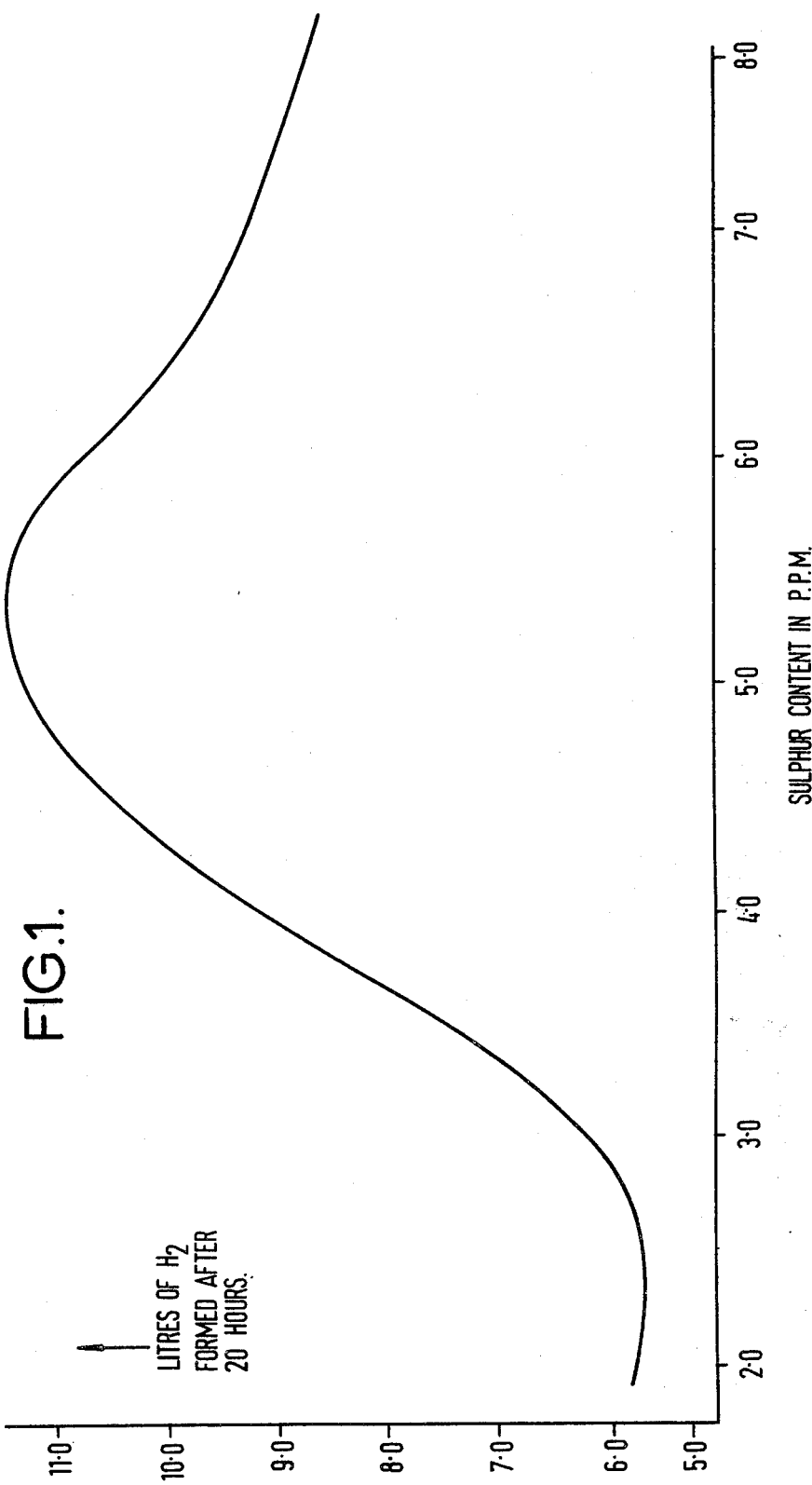

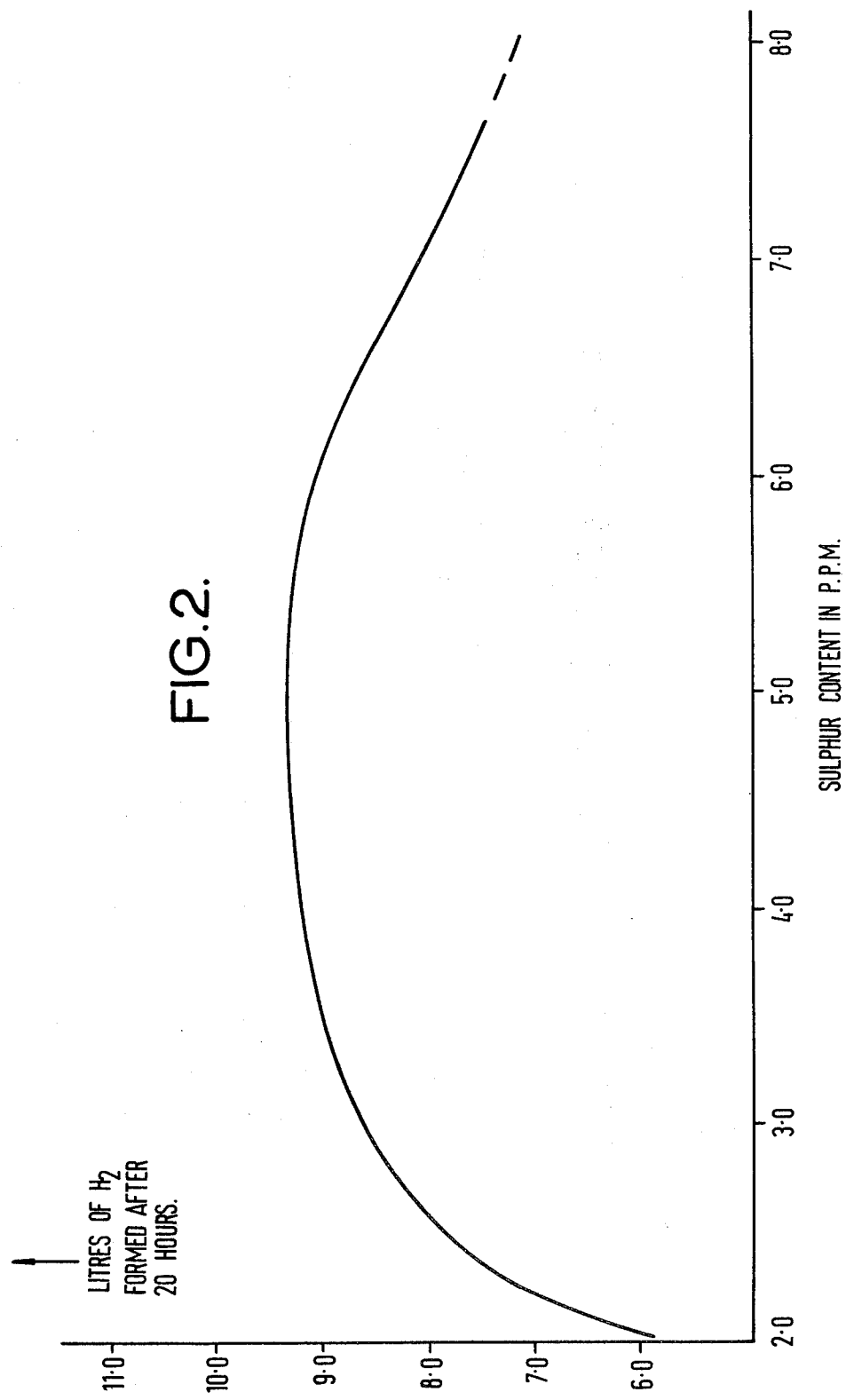

PROCESS FOR THE PRODUCTION OF O-PHENYLPHENOL

This invention relates to methods of preparing o-phenyl phenols.

o-phenyl phenols are generally prepared in a two-stage process from cyclohexanones. In the first stage, the cyclohexanone is condensed in the presence of a catalyst to form o-cyclohexenyl cyclohexanone, otherwise called 2-(1-cyclohexenyl) cyclohexanone. This product is then removed from the reaction mixture and, in the second stage, is dehydrogenated in the presence of a suitable dehydrogenation catalyst to form the o-phenyl phenol. This sequence is illustrated for cyclohexanone itself by the following reactions:

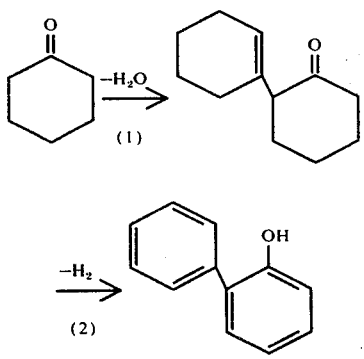

The first stage is most conveniently effected by homogeneous catalysis in the liquid phase, and may be carried out in the presence of any one of several catalysts, for example mineral acids, such as sulphuric acid, hydrochloric acid and phosphoric acid, or alkalis, such as sodium hydroxide. A series of alternative catalysts for this first stage are disclosed and claimed in British Patent Specification No. 1249473. These catalysts contain one or more of the heavy metals titanium, vanadium, chromium, manganese, iron, cobalt, nickel, copper, zirconium, cadmium or tin, usually as an organic compound, particularly the salt of an organic acid, e.g., aliphatic carboxylic acids or naphthenic acids.

The second stage is a conventional dehydrogenation which is carried out in the presence of any suitable dehydrogenation catalyst, such as palladium or platinum or an inert support, for example charcoal or alumina.

The heavy metal salts of organic acids are used as catalysts in the first stage are conveniently based on complex mixtures of mainly monocarboxylic acids of various hydrocarbon series which occur in and are derived from petroleum.

In view of the decreasing availability of petroleum-based products, attempts have been made to use other catalysts in the preparation of the intermediate o-cyclohexenyl cyclohexanone. However it has been observed that the o-cyclohexenyl cyclohexanones prepared using these alternative catalysts cannot be converted to the o-phenyl phenols with the same efficiency as those o-cyclohexenyl cyclohexanones prepared using the conventional catalysts. Thus, in experiments which we have performed using o-cyclohexenyl cyclohexanone which had been prepared with a sulphuric acid condensation catalyst, the proportion of o-phenyl phenol contained in the reaction products obtained from a dehydrogenation over palladium-charcoal only reached 60% after a period of 22 hours. This yield was so low that separation of this product from the by-products would not have been practicable on a commercial scale.

As a result of experimental work which we have performed on the dehydrogenation of o-cyclohexenyl cyclohexanones to o-phenyl phenols we have found that the catalyst for the dehydrogenation can be selectively poisoned so that it consistently produces o-phenyl phenol as the major dehydrogenation product by carrying out the dehydrogenation in the presence of traces of sulphur. All naphthenic acids, and therefore all their heavy metal salts, contain traces of sulphur compounds, and we believe that the success of the dehydrogenation of o-cyclohexenyl cyclohexanones prepared using heavy metal naphthenate catalysts compared with the dehydrogenation of the o-cyclohexenyl cyclohexanones prepared using other catalysts is attributable to the fact that the former cyclohexanones inevitably contain sufficient traces of sulphur after removal from the naphthenic acid salt to poison the dehydrogenation catalyst used in the subsequent stage of the reaction to the required extent.

In accordance with the present invention, therefore, we provide a method of preparing an o-phenyl phenol which comprises forming an o-cyclohexenyl cyclohexanone from a cyclohexanone by condensing the cyclohexanone in the presence of a condensation catalyst other than a naphthenate, and dehydrogenating the resulting o-cyclohexenyl cyclohexanone by contacting the o-cyclohexenyl cyclohexanone with a dehydrogenation catalyst in the presence of sufficient sulphur in the form of elemental sulphur or an organo-sulphur compound to improve the selectivity of the dehydrogenation catalyst with respect to the formation of o-phenyl phenol.

Stated another way, the invention provides a method of preparing an o-phenyl phenol which comprises the steps of forming an o-cyclohexenyl cyclohexanone from a cyclohexanone by condensing the cyclohexanone in the presence of an inherently sulphur-free condensation catalyst, and then dehydrogenating the resulting o-cyclohexenyl cyclohexanone by contacting the o-cyclohexenyl cyclohexanone with a dehydrogenation catalyst in the presence of sufficient sulphur in the form of elemental sulphur or an organo-sulphur compound to improve the selectivity of the dehydrogenation catalyst with respect to the formation of o-phenyl phenol.

The term "inherently sulphur-free catalyst" is intended to exclude those catalysts, such as the heavy metal naphthenates, which inevitably contain sulphur in elemental form or in the form of a carbonaceous compound such as a sulphide or a thiol. The term does not exclude the inorganic sulphur-containing catalysts, such as sulphuric acid. Thus our invention includes the use of any of the conventional sulphur-free condensation catalysts in the first stage of the preparation, e.g. any of the sulphur-free compounds disclosed in British patent specification No. 1249473, an acid or a base. Examples of these sulphur-free catalysts are organic compounds of tin, cobalt, vanadium or titanium, e.g. tetrabutyl titanate, acids, such as sulphuric acid, and bases, such as sodium hydroxide. Sulphuric acid is preferred as the condensation catalyst in view of its low cost. Any dehydrogenation catalyst may be used, the noble metals (i.e., ruthenium, rhodium, osmium, iridium, platinum, and palladium) being particularly useful, especially platinum and palladium. In practice when a noble metal is used, it will be supported on an inert carrier such as carbon, alumina or silica.

The quantity of sulphur present in the dehydrogenation step is extremely critical, and the selectivity of the dehydrogenation catalyst is impaired if either too much or too little sulphur is present.

The exact quantity of sulphur which may be used in the dehydrogenation step to achieve the optimum selectivity in the catalyst depends upon the chemical form in which the sulphur is added and on the catalyst itself. However the optimum amount of sulphur can easily be determined by routine experiments similar to those described in the following Examples. As a general guide, where a palladium or platinum dehydrogenation catalyst is used, an improvement in the selectivity of the catalyst with respect to o-phenyl phenol will usually be observed using a sulphur/metal weight ratio of from 1/60 to 1/12, often between 1/40 and 1/20, in the dehydrogenation. Thus, if a 5% palladium/charcoal catalyst is used in the dehydrogenation, in an amount of 2500 parts by weight per million (ppm), the quantity of sulphur required to produce an improvement in the selectivity of the catalyst will usually lie between 2 and 10 ppm, depending on the form in which the sulphur is added. If the sulphur is added in the form of the element, dodecane-1-thiol or naphthenic acid, from 3 to 8 ppm of sulphur will be required with this dehydrogenation catalyst, the best results being obtained with from 4 to 7 ppm of sulphur. If however, the sulphur is added as diphenyl sulphide, the best improvement in the selectivity of this catalyst is obtained using from 3 to 6 ppm of sulphur. These figures would of course vary if a different quantity of catalyst were used or if a similar catalyst of different metal/support, e.g., charcoal, ratio were used.

One possible way in which the sulphur may be introduced into the dehydrogenation stage of the reaction is by adding or forming a suitable sulphur-containing compound in the first stage of the reaction and removing the sulphur-containing compound and the o-cyclohexenyl cyclohexanone from the reaction mixture together by distillation. It may then be necessary to supplement the sulphur content of the o-cyclohexenyl cyclohexanone prior to the dehydrogenation. This procedure is adopted when sulphuric acid is used in the first stage of the reaction. The distillate from this first stage is found to contain about 2 ppm sulphur in the form of organo-sulphur compounds produced by side-reactions.

Where the distillate from the first stage is free from sulphur however, all the organo-sulphur compound or elemental sulphur is added in a single batch immediately prior to the catalytic dehydrogenation.

The sulphur may be in the elemental form, or in the form of an organic compound such as a thiol, a sulphide or a naphthenate. Inorganic sulphur compounds such as sulphuric acid are however ineffective in the selective poisoning of the dehydrogenation catalyst. Examples of suitable organo-sulphur compounds are alkyl and aryl sulphides, thiols, such as dodecane-1-thiol and those contained in naphthenic acid and aromatic sulphur-containing compounds such as diphenyl sulphide. Elemental sulphur is the preferred additive.

The conditions under which the two stages of the process are carried out are conventional, and will be known to any person skilled in this field. Typically, the first stage of the reaction is carried out by adding the condensation catalyst to the cyclohexanone and heating the mixture for a period of time. The time, temperature and the quantity of catalyst used will depend upon the nature of the catalyst. Thus if a heavy metal compound such as tetrabutyl titanate is used, a reaction time of 2½ hours under reflux will be satisfactory with a catalyst concentration of 1% by weight. For caustic soda the reaction time is about the same with a concentration of 0.15%. However with sulphuric acid, the concentration should be 10% by weight, the reaction temperature 90°–100° C and the time 30 minutes.

The o-cyclohexenyl cyclohexanone is removed from the reaction mixture, preferably by distillation, and is then usually heated with the dehydrogenation catalyst in the presence of the sulphur for a period of from 20 to 25 hours at reflux temperature. The quantity of dehydrogenation catalyst used will normally be from 2000 to 3000 ppm by weight of a supported catalyst containing 5% by weight of noble metal.

In order that the invention may be better understood, particular embodiments thereof will be described in the following Examples, in which all proportions are by weight:

EXAMPLES 1 TO 7

For each of these examples, a sample of o-cyclohexenyl cyclohexanone was prepared as follows:

500 gm of cyclohexanone was mixed with 100 gm of 50% sulphuric acid. This homogeneous mixture was heated under a nitrogen atmosphere and with stirring to 90°–100° C, and held at that temperature for 20 minutes. During the heating, a second phase appeared when the temperature reached about 70° C.

At the end of the reaction period the phases were separated and the upper organic phase was neutralized with a solution of sodium carbonate. The aqueous phase was discarded and the organic phase washed with water (50 ml). Water was removed from the organic phase by azeotropic distillation and the product was separated by distillation into o-cyclohexenyl cyclohexanone (170 gm) and cyclohexanone for recycle. Analysis of the product showed approximately 2 ppm of sulphur as organo-sulphur compounds.

The aqueous phase at the end of the reaction period contained sulphuric acid and a substantial amount of organic material (cyclohexanone and o-cyclohexenyl cyclohexanone). It was therefore made up with fresh sulphuric acid and used in the preparation of the next batch.

EXAMPLE 1

20 gm of the o-cyclohexenyl cyclohexanone were heated under reflux at a temperature of 280° C with 50 mg of a 5% palladium/charcoal dehydrogenation catalyst and the volume of hydrogen evolved from the mixture over a period of 20 hours was collected and measured. The quantity evolved was a measure of the extent to which the o-cyclohexenyl cyclohexanone had been dehydrogenated. Since a complete dehydrogenation of 20 gm of o-cyclohexenyl cyclohexanone to o-phenyl phenol would have produced 10.1 liters of hydrogen (measured at N.T.P.) and o-phenyl phenol is the ultimate reduction product of o-cyclohexenyl cyclohexanone (apart from dibenzfuran, which was shown to be formed in the reaction only to a small extent) the quantity of hydrogen produced is a measure of the selectivity of the catalyst with respect to the formation of o-phenyl phenol. In fact 4.3 liters of hydrogen (at N.T.P.) were produced, which indicates a poor selectivity. This was confirmed by gas-liquid chromatographic analysis of the reaction products, which revealed 58.7% of o-phenyl phenol, or 60% of the theoretical yield.

EXAMPLES 2 TO 6

The dehydrogenation procedure of Example 1 was repeated in the presence of different quantities of sulphur. The 2 ppm sulphur already present in the o-cyclohexenyl cyclohexanone was supplemented by adding various quantities of naphthenic acid, which itself contains 0.55% by weight of sulphur. The volume of hydrogen evolved in each case was measured, and the reaction products analyzed by gas-liquid chromatography, and infra-red spectroscopy. The details and the results of the experiments are summarized in Table 1.

Table 1

| Ex. No. | Naphthenic acid added % | Total Sulphur Content ppm | Pd:S weight ratio | Hydrogen evolved in liters at N.T.P. | Yield of o-phenyl phenol % |
|---|---|---|---|---|---|
| 2 | 0.01 | 2.50 | 1:20 | 4.3 | ~60 |
| 3 | 0.025 | 3.37 | 1:27.2 | 5.6 | 85 |
| 4 | 0.064 | 5.52 | 1:44 | 9.6 | >98 |
| 5 | 0.073 | 6.01 | 1:48 | 8.6 | 98 |
| 6 | 0.100 | 7.50 | 1:56 | 7.3 | ~95 |

FIG. 1 is a graph showing the variation of the quantity of hydrogen evolved with the quantity of sulphur used in the dehydrogenation.

EXAMPLES 7 TO 10

The same procedure as described in Examples 2 to 6 was adopted, the sulphur being added in the form of diphenyl sulphide. The details and the results of the experiments are summarized in Table 2.

Table 2

| Ex. No. | Diphenyl Sulphide added ppm | Total Sulphur Content ppm | Pd:S weight ratio | Hydrogen evolved in liters at N.T.P. | Yield of o-phenyl phenol % |
|---|---|---|---|---|---|
| 7 | 17.4 | 3.0 | 1:24 | 7.3 | 90 |
| 8 | 26.2 | 4.5 | 1:30 | 7.9 | 94 |
| 9 | 32.0 | 5.5 | 1:44 | 7.9 | >95 |
| 10 | 40.7 | 7.0 | 1:56 | 6.8 | 93 |

FIG. 2 is a graph similar to FIG. 1. A comparison of FIGS. 1 and 2 shows that the palladium catalyst is less sensitive to the presence of sulphur in the form of diphenyl sulphide than to sulphur in the form of naphthenic acid and that diphenyl sulphide remains effective at lower concentrations than naphthenic acid.

EXAMPLES 11 TO 15

The dehydrogenation procedure of Example 1 was repeated in each of these examples in the presence of 6 ppm total sulphur, the 2 ppm sulphur already present in the o-cyclohexenyl cyclohexanone being supplemented from a different source of sulphur. The details and results of the experiments are summarized in Table 3.

Table 3

| Example No. | Sulphur added as | Hydrogen evolved in liters at N.T.P. | Yield of o-phenyl phenol % |
|---|---|---|---|
| 11 | Naphthenic acid | 9.6 | >98 |
| 12 | Dodecanel-1-thiol | 8.9 | 96 |
| 13 | Sulphur | 8.7 | 97 |
| 14 | Diphenyl sulphide | 7.9 | >95 |
| 15 | Sulphuric acid | 4.0 | ~30 |

These results show that added sulphur in the form of sulphuric acid has an adverse effect on the selectivity of the palladium catalyst and that naphthenic acid is the most effective additive. The next best additive is elemental sulphur which was introduced into the system by heating in the o-cyclohexenyl cyclohexanone to form a solution before the palladium catalyst was added.

EXAMPLES 16 TO 19

For the following examples, samples of o-cyclohexenyl cyclohexanone were prepared by heating 500 gm of cyclohexanone under reflux for 2.75 hours with 0.75 gm of sodium hydroxide. The resulting mixture was distilled under vacuum to yield 204 gm of o-cyclohexenyl cyclohexanone. Analysis of a sample of the product revealed that is contained no sulphur.

A 20 gm sample of the o-cyclohexenyl cyclohexanone thus obtained under reflux at a temperature of 280° C with 50 mg of a 5% palladium/charcoal dehydrogenation catalyst for 20 hours, and the volume of hydrogen evolved in that period was determined. The product of the reaction was analyzed by gas-liquid chromatography. This procedure was then repeated in the presence of sulphur-containing additives. The details and the results of the experiments are set out in Table 4.

Table 4

| Example No. | Additive | Sulphur concentration ppm | Hydrogen evolved in liters at N.T.P. | Yield of o-phenyl phenol % |
|---|---|---|---|---|
| 16 | none | 0 | 3.9 | 60 |
| 17 | naphthenic acid | 3.9 | 8.3 | 98 |
| 18 | dodecane thiol | 3.5 | 8.3 | 95 |
| 19 | sulphur | 5.5 | 8.7 | 95 |

We claim:
1. In a method of preparing an O-phenyl phenol from a cyclohexanone which comprises the steps of
   a. condensing the cyclohexanone in the presence of a condensation catalyst other than a naphthenate to form a reaction mixture containing an O-cyclohexenyl cyclohexanone,
   b. removing the O-cyclohexenyl cyclohexanone from the reaction mixture, and
   c. dehydrogenating the O-cyclohexenyl cyclohexanone from step (b) by contacting it with a noble metal dehydrogenation catalyst, selected from the group consisting of ruthenium, rhodium, osmium, iridium, platinum and palladium, the improvement wherein the dehydrogenation step is conducted in the presence of sulphur in the form of elemental sulphur or organo-sulphides or thiols, the sulphur/dehydrogenation catalyst metal weight ratio being from about 1/60 to 1/12, to improve the selectivity of the said dehydrogenation catalyst with respect to the formation of O-phenyl phenol.

2. In a method of preparing an O-phenyl phenol from a cyclohexanone which comprises the steps of
   a. condensing the cyclohexanone in the presence of an inherently sulphur-free condensation catalyst to form a reaction mixture containing an O-cyclohexenyl cyclohexanone,
   b. removing the O-cyclohexenyl cyclohexanone from the reaction mixture, and
   c. dehydrogenating the O-cyclohexenyl cyclohexanone from step (b) by contacting it with a noble metal dehydrogenation catalyst, selected from the group consisting of ruthenium, rhodium, osmium, iridium, platinum and palladium, the improvement wherein the dehydrogenation step is conducted in the presence of sulphur in the form of elemental sulphur or organo-sulphides or thiols, the sulphur/dehydrogenation catalyst metal weight ratio being from about 1/60 to 1/12, to improve the selectivity of the said dehydrogenation catalyst with respect to the formation of O-phenyl phenol.

3. The method of claim 2, wherein the organic-sulphide and/or -thiol is present as an impurity in naphthenic acid.

4. The method of claim 2, wherein at least a portion of the organo-sulphite and/or thiol is introduced by carry-over from step (a).

5. The method of claim 2, wherein said sulphur-free catalyst is an organic compound of cobalt, vanadium, tin or titanium, an acid or a base.

6. The method of claim 5, wherein said essentially sulphur free catalyst is sulphuric acid.

7. The method of claim 5, wherein said sulphur-free catalyst is sodium hydroxide.

8. The method of claim 2 wherein sufficient sulphur is present at the dehydrogenation step to give a sulphur/catalyst metal weight ratio of 1/60 to 1/12.

9. The method of claim 2, wherein at least a portion of the sulphur is introduced into the dehydrogenation stage by carry-over of an organo-sulphur compound generated in step (a).

* * * * *